(12) United States Patent
Brioni et al.

(10) Patent No.: US 6,323,231 B1
(45) Date of Patent: Nov. 27, 2001

(54) USE OF $\alpha_{1A}$ ADRENOCEPTOR AGONISTS WITH $\alpha_{1B}$ AND $\alpha_{1D}$ ANTAGONISM FOR THE TREATMENT OF STRESS URINARY INCONTINENCE

(75) Inventors: Jorge D. Brioni, Vernon Hills; Michael E. Brune, Mundelein; Steven A. Buckner, Wadsworth; Teodozyj Kolasa, Lake Villa; James P. Sullivan, Deerfield, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/788,198

(22) Filed: Feb. 16, 2001

Related U.S. Application Data
(60) Provisional application No. 60/183,498, filed on Feb. 17, 2000.

(51) Int. Cl.$^7$ .................................................. A61K 31/415
(52) U.S. Cl. .............................................................. 514/400
(58) Field of Search ............................................. 514/400

(56) References Cited

U.S. PATENT DOCUMENTS

| | | |
|---|---|---|
| 5,610,174 | 3/1997 | Craig et al. . |
| 5,686,425 * | 11/1997 | Lee ........................................ 514/21 |
| 5,952,362 | 9/1999 | Cournoyer et al. . |
| 6,057,349 * | 5/2000 | Cournoyer et al. .................. 514/365 |

FOREIGN PATENT DOCUMENTS

| | | |
|---|---|---|
| 0538469 | 4/1998 | (EP) . |
| 0887346 | 12/1998 | (EP) . |
| 9402442 | 2/1994 | (WO) . |
| 9632939 | 10/1996 | (WO) . |
| 9638143 | 12/1996 | (WO) . |
| 9842679 | 10/1998 | (WO) . |
| 9957131 | 11/1999 | (WO) . |
| 0007997 | 2/2000 | (WO) . |

OTHER PUBLICATIONS

Aboud, R. et al., Br. J. Pharmacol 109:80–87 (1993).
Arunlakshana, O. et al., Br. J. Pharmacol. 14:48–58 (1959).
Bridgewater, M. et al., Journal of Urology 150:223–228 (1993).
Brune, et al., Drug Development Research 34:267–275 (1995).
Cavalli, a. et al., Proceedings of the National Academy of Sciences USA 94:11589–11594 (1997).
Chapple, C. et al., British Journal of Urology 63:487–496 (1989).
Chess–Williams, R. et al., Journal Autonomic Pharmacology 14:375–381 (1994).
Collste, L. et al., Urology 30:398–403 (1987).
DeGroat, et al., European Urology, v36(suppl:68–73 (1999) abstract.
DeLean, A. et al., Am. J. Physiol. 235:E97–102 (1980).
Docherty, J. R., "Subtypes of functional $\alpha_1$–and $\alpha_2$–adrenoceptors", Eur. Journ. of Pharm., 361:1–15 (1998).
Hancock, A., Drug Development Research 39:54–107 (1996).
Hieble, J. P., et al., "Subclassification and nomenclature of $\alpha_1$–and $\alpha_2$–adrenoceptors", Prog. In Drug Research, 47:81–130 (1996).
Knepper, et al., J. Pharm Exp. Ther. 274:97–103 (1995).
Lehtonen, T. et al., "The effect of Phenylpropanol on Female Stress Urinary Incontinence," Annales Chiruglae et Gynaecologiae 75:236–241 (1996).
Martin, D. J., et al., "Functional Uroselectivity", Eur. Urol., 33(2):12–18 (1998).
Nishi, K. et al., Jouranl of Urology 160:196–205 (1998).
Ruffolo, Jr., R. R., et al., "$\alpha$–and $\beta$–Adrenoceptors: From the Gene to the Clinic. 2. Structure–Activity Relationships and Therapeutic Applications", Journ of Medicinal Chemistry, 38(19):3681–3716 (1995).
Schild, H.O., Br. J. Pharmacol. 2:189–206 (1947).
Schorn, T. et al., "T. alpha–1d adrenergic receptor (AR) subtype contributes to the phenylephrine (PE)–induced increase in canine prostatic intraurethral pressure (IUP)" Faseb Journal 13(4)Part 1:A142(1999).
Sommers, W. et al., Journal of Urology 141:1230–1233 (1989).
Testa, R. et al., European Journal of Pharmacology 249:307–315 (1993).
Wein, A., Urologic Clinics of North America 22:557–577 (1995).
Zhong, H., et al., "$\alpha_1$–Adrenoceptor subtypes", Eur. Journ. of Pharm., 375:261–276 (1996).
Zielinski, P.J. et al., Analyst, 123:1661–1668 (1998).

* cited by examiner

Primary Examiner—Raymond Henley, III
(74) Attorney, Agent, or Firm—Michael J. Ward

(57) ABSTRACT

The following disclosure relates to a method of treating incontinence with a compound having a specific $\alpha_{1A}$ adrenoceptor profile.

6 Claims, 1 Drawing Sheet

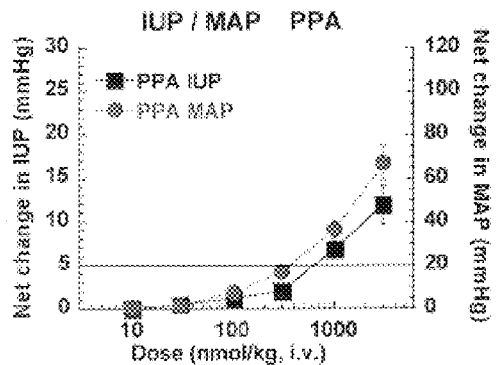

Figure 1: Effect of phenylpropanolamine on intraurethral pressure (IUP) and mean arterial pressure (MAP) in dogs after i.v. administration of the compound.

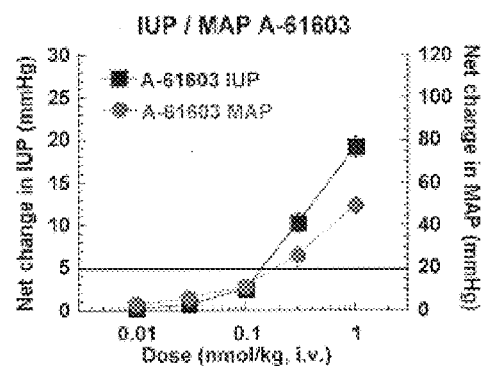

Figure 2: Effect of A-61603 on intraurethral pressure (IUP) and mean arterial pressure (MAP) in dogs after i.v. administration of the compound.

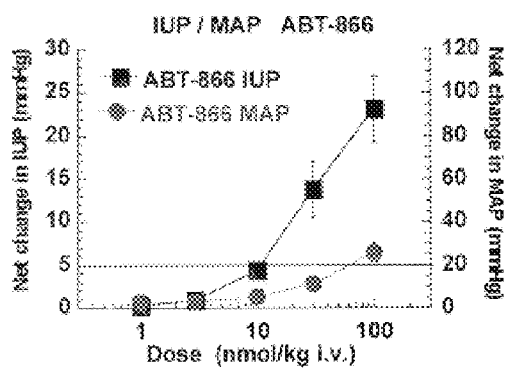

Figure 3: Effect of A-286569 on intraurethral pressure (IUP) and mean arterial pressure (MAP) in dogs after i.v. administration of the compound.

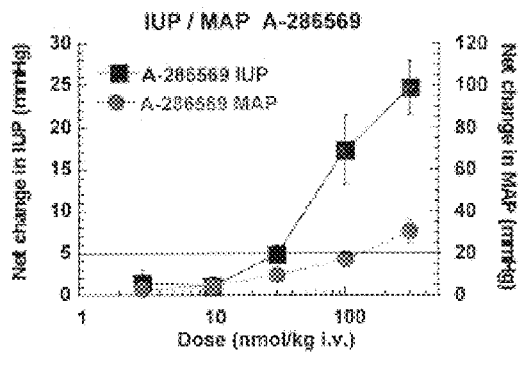

Figure 4: Effect of A-286569 on intraurethral pressure (IUP) and mean arterial pressure (MAP) in dogs after i.v. administration of the compound.

USE OF $\alpha_{1A}$ ADRENOCEPTOR AGONISTS WITH $\alpha_{1B}$ AND $\alpha_{1D}$ ANTAGONISM FOR THE TREATMENT OF STRESS URINARY INCONTINENCE

REFERENCE TO RELATED APPLICATION

This application is a conversion of U.S. Provisional Application No. 60/183,498, filed on Feb. 17, 2000.

TECHNICAL FIELD

The present invention discloses a novel approach in the treatment of stress urinary incontinence. More specifically, this invention provides a method of treating urinary incontinence by administering selective $\alpha_{1A}$ adrenoceptor agonists with antagonistic properties at the $\alpha_{1B}$ and $\alpha_{1A}$ subtypes.

BACKGROUND OF THE INVENTION

Urinary incontinence is a condition defined as the involuntary loss of urine and was recently classified as a disease by the World Health Organization. Involuntary loss of urine occurs when pressure inside the bladder exceeds the retentive pressure of the urethral sphincters (intraurethral pressure). The disease may arise from different pathological, anatomical and neurological factors. Three major types of urinary incontinence have been defined based on symptoms, signs and condition: stress, urge and mixed incontinence.

Stress urinary incontinence (SUI) is the involuntary loss of urine during coughing, sneezing, laughing, or other physical activities that increase intra-abdominal pressure in the absence of a bladder contraction. SUI is most common in women between the ages of 25 and 50, and up to 47% of regularly exercising women have some degree of SUI.

The most common causes of SUI in women are urethral hypermobility and intrinsic urethral sphincter deficiency. Urethral hypermobility is characterized by a weakness of the pelvic floor support. Because of this weakness, there is rotational descent of the bladder neck and proximal urethra during increases in abdominal pressure. If the urethra opens concomitantly, SUI may ensue. Intrinsic urethral sphincteric deficiency denotes a dysfunction of the urethral smooth and striated muscle support system. This may have congenital origins, or may be acquired after surgery, trauma, or a sacral cord lesion. In females, intrinsic urethral sphincter deficiency is commonly associated with multiple incontinence surgical procedures, as well as hypoestrogenism, aging or both. In this condition, the urethral smooth muscle and sphincter is unable to generate enough resistance to retain urine in the bladder, especially during the stress maneuvers. It is believed that a number of patients suffer from both urethral hypermobility and intrinsic urethral sphincter deficiency.

The present methods to treat SUI include physiotherapy and surgery. Treatment with pharmaceutical agents is limited to the use of non-selective adrenergic agonists like phenyl-propanolamine and midodrine. The rationale for the use of adrenergic agonists for the treatment of SUI is based on physiological data indicating an abundant noradrenergic input to smooth muscle of the urethra. Studies in rats, cats and dogs indicate that sympathetic adrenergic input to the urethra is tonically active during bladder filling to promote urine storage, and that surgical or pharmacological blockade of the sympathetic pathways can reduce urethral resistance.

Substantial preclinical physiological, pharmacological and molecular evidence suggests that $\alpha_{1A}$ adrenoceptors are responsible for mediating the effects of norepinephrine on urethral tone. Receptor binding and autoradiographic studies have revealed the existence of $\alpha_1$ adrenoceptors in human, rabbit and dog urethra (Chapple C, Aubry M, James S, Greengrass P, Burnstock G, Turner-Warwick R, Milroy E and Davey M (1989). Characterisation of human prostatic adrenoceptors using pharmacology receptor binding and localization. British Journal of Urology 63: 487–496; Testa R, Guarnieri L, Ibba M, Strada G, Pogessi E, Taddei C, Simonazzi I and Leonardi A (1993). Characterization of alpha-1 adrenoceptor subtypes in prostate and prostatic urethra of rat, rabbit dog and man.

European Journal of Pharmacology 249: 307–315; Nishi K, Latifpour J, Saito M, Foster H, Yoshida M and Weiss R (1998). Characterization, localization and distribution of α1 adrenoceptor subtype in male rabbit urethra. Journal of Urology 160: 196–205), and in vitro studies demonstrated that the cc, receptors regulate urethral tone as phenylephrine can contract isolated urethral strips from several animal species (Bridgewater M, MacNeil H and Brading A (1993). Regulation of tone in pig urethral smooth muscle. Journal of Urology 150: 223–228; Chess-Williams R, Aston N and Couldwell C (1994). α1 A-adrenoceptor subtype mediates contraction of the rat urethra. Journal Autonomic Pharmacology 14: 375–381). Isolated strips of human urethral muscle also contract in response to $\alpha_1$ adrenoceptor agonists, a response that is blocked by $\alpha_1$ antagonists like prazosin (Brading A, Fry C, Maggi C, Takeda M, Wammack R, Wicklund N, Uvelius B and Gabella G (1998). Incontinence: Cellular Biology. In: Incontinence (Eds. Abrams P, Khoury S and Wein A), pp. 59–104, Monaco; Chapple 1989). Similarly, systemic injections of epinephrine increase intraurethral pressure in anesthetized dogs, an effect also blocked by prazosin (Sommers W, Felsen D, Chou T, Marion D, Chernesky C and Darracott-Vaughan E (1989). An in vivo evaluation of alpha adrenergic receptors in canine prostate. Journal of Urology 141: 1230–1233).

Adrenoceptors are cell membrane receptors belonging to the heptahelical G-protein family of receptors (GPCRs) that respond to the physiological agonists, norepinephrine and epinephrine (Hancock A (1996). α1 adrenoceptor subtypes: A synopsis of their pharmacology and molecular biology. Drug Development Research 39: 54–107). They are divided into 3 families: $\alpha_1$, $\alpha_2$ and $\beta$. Although α adrenoceptors were originally subclassified into "$\alpha_1$ postsynaptic" and "$\alpha_2$ presynaptic", this purely anatomical classification was later abandoned and defined based on the pharmacology and the molecular biology of the cloned receptors (Langer S (1999). History and nomenclature of α1-adrenoceptors. European Urology 36: 2–6). Six genes have been identified and sequenced to support the present classification: $\alpha_{1a}$, $\alpha_{1b}$, $\alpha_{1d}$, $\alpha_{2b}$, and $\alpha_{2c}$ (as recommended by IUPHAR, lowercase subscripts designate the cloned subtypes, and uppercase subscripts define the pharmacologically defined subtypes). The elucidation of the molecular diversity of adrenoceptors has provided a molecular correlate to earlier pharmacological studies. The use of subtype specific probes has shown that the human, dog and rabbit urethra are enriched with mRNA for the $\alpha_{1A}$ adrenoceptor, and RNAase protection assays indicated that the $\alpha_{1a}$ subtype is the predominant subtype in human urethra.

Clinical studies with the non-selective a adrenoceptor agonists, PPA and midodrine have demonstrated limited clinical efficacy. The use of PPA has been limited by concerns regarding dose-limiting side effects, particularly hypertension, that have curtailed the ability to evaluate the compound at higher doses. PPA is a non-selective adrenergic agonist lacking selectivity for $\alpha_1$, adrenoceptors in tissue bath studies. Several patents like EP 887,346; EP 538,469 and U.S. Pat. No. 5,610,174 disclose compounds that are claimed as selective $\alpha_{1A}$ adrenoceptor agonists.

Adrenergic receptors in the vascular bed regulating blood pressure are presumed to be mainly of the $\alpha_{1B}$ subtype. Adrenergic antagonists (like prazosin and terazosin) reduce blood pressure in Spontaneously Hypertensive rats (SHRs) with a potency ranking that correlates with their potency to displace binding to the $\alpha_{1b}$ receptor but not the $\alpha_{1a}$ receptor (Hancock 1996), and a reduced hypertensive response to phenypephrine has been observed in $\alpha_{1b}$ knock-out mice (Cavalli A, Lattion A, Hummler E, Nonniger M, Pedrazzini T. Aubert J, Michel M, Yang M, Lembo G, Vecchione C, Mostardini M, Schmidt A, Beerman F and Cotecchia S (1997). Decreased blood pressure response in mice deficient of the α1-adrenergic receptor. *Proceedings of the National Academy of Sciences USA* 94:11589–11594). However, there is recent data to suggest that $\alpha_{1A}$ receptors may also exist extra-synaptically in the vasculature, and while such receptors may not be involved in the normal regulation of blood pressure they may respond to exogenous $\alpha_{1A}$ agonists. Based on these data, the $\alpha_{1B}$ antagonist attributes may reduce the hypertensive liability of the $\alpha_{1A}$ adrenergic agonists.

The $\alpha_1$ receptors in the bladder are mainly the $\alpha_{1D}$ subtype. Adrenergic antagonists like prazosin decrease bladder hyperreflexia and increase bladder capacity (Andersson K (1999). α1-adrenoceptors and bladder function. *European Urology* 36: 96–102). In view of these clinical findings, $\alpha_{1D}$ antagonism may provide additional benefit to patients with mixed incontinence.

There continues to be a need for medicaments that are useful for treating incontinence. A compound having the desired $\alpha_{1A}$ agonist and $\alpha_{1B}$ and preferably $\alpha_{1D}$ antagonist profile may be useful in treating incontinence.

SUMMARY OF THE INVENTION

The present invention provides a method of treating stress urinary incontinence by providing to the subject a compound having $\alpha_{1A}$ adrenoceptor agonistic properties as well as antagonistic properties at $\alpha_{1B}$ and preferably $\alpha_{1D}$ adrenoceptors.

BRIEF DESCRIPTION OF THE DRAWINGS

FIG. 1: Demonstrates the effect of phenylpropanolamine on intraurethral pressure (IUP) and mean arterial pressure (MAP) in dogs after i.v. administration of the compound.

FIG. 2: Demonstrates the effect of A-61603 on intraurethral pressure (IUP) and mean arterial pressure (MAP) in dogs after i.v. administration of the compound.

FIG. 3: Demonstrates the effect of A-286569 on intraurethral pressure (IUP) and mean arterial pressure (MAP) in dogs after i.v. administration of the compound.

FIG. 4: Demonstrates the effect of A-286569 on intraurethral pressure (IUP) and mean arterial pressure (MAP) in dogs after i.v. administration of the compound.

DETAILED DESCRIPTION OF THE INVENTION

All references cited within this document are hereby incorporated by reference.

The present invention provides a method of treating stress urinary incontinence by administering selective $\alpha_{1A}$ adrenoceptor agonists with $\alpha_{1A}$ and preferably $\alpha_{1D}$ antagonistic properties. The invention provides a method of inducing contraction of the urethra and bladder neck via the effect of administering a compound that is a $\alpha_{1A}$ adrenoceptor agonist, and also provide a method to block $\alpha_{1B}$ adrenoceptors present in the vascular tissue and also preferably block $\alpha_{1D}$ adrenoceptor in the bladder. One of the goals of the present invention is to provide a means for developing compounds for treating incontinence by getting better separation in intrauretheral pressure versus mean arterial pressure. Preferably compounds have an IUP (5 mmHg)/MAP (20 mmHg) selectivity ratio of 5 or greater. More preferably, compounds have an IUP (5 mmHg)/MAP (20 mmHg) selectivity ratio of 10 or greater.

Pharmacological treatment of stress urinary incontinence is presently focused on the use of non-selective α agonists or by using selective $\alpha_{1A}$ adrenoceptor agonists. These type of compounds may induce an increase in mean arterial pressure that limits the therapeutic use of present drugs The use of compounds having $\alpha_{1A}$ adrenoceptor agonistic activity together with $\alpha_{1B}$ antagonistic properties may provide a superior urethral-vascular selectivity. The $\alpha_{1B}$ antagonism may reduce the potential hypertensive side-effects. Administration of a compound exhibiting $\alpha_{1B}$ antagonism may provide additional benefit by ameliorating the constriction of vascular tissue typically associated with the use of non-selective α agonists. It is to be understood that the compounds having the desired profile may be administered by oral, intra-venous, subcutaneous, and intramuscular means.

Quantitative analysis of agonist and antagonist action is the basis of receptor classification and drug design. When an "agonist" binds to a compatible receptor it forms an agonist-receptor complex and initiates a second messenger event resulting in either contraction of smooth muscle or relaxation depending on the receptor type and or location. The interaction of an agonist with a receptor may be characterized by two quantities, affinity and efficacy. These quantities can be estimated by generating two concentration response curves and fitting the data to a four parameter curve smoothing routine. The first curve is a reference standard followed by a thorough rinsing and a second curve generated using the test agent. From this data the affinity (potency) described as an $EC_{50}$ (half maximum response) can be determined. Agonist potency ($pD_2$) is expressed as the negative log 10 of the $EC_{50}$. The efficacy is determined by comparing the maximum value of the test agent to the maximum value of the reference agent and expressed as a % of maximum response. For purposes of this disclosure, agonists which exhibit less than 25% agonism as compared to phenylephrine are not considered agonists.

Conversely, an "antagonist" blocks the receptor from binding to an agonist and therefore prevents intracellular responses which lead to contraction of smooth muscle or relaxation depending on the receptor type and or location. The interaction of an antagonist with a receptor can be characterized by an affinity constant, $pA_2$. The affinity unit, $pA_2$, can be defined as negative logarithm to base 10 of the molar concentration of antagonist drug that will reduce the effect of the reference agonist by 50%. Three analytical criteria that competitive antagonists possess should be satisfied The fractional increase in agonist concentration required to overcome the effects of the antagonist should be independent of the agonist concentration. Secondly, the affinity of the antagonist should be independent of concentration, therefore the Schild plot should have a slope of unity. Thirdly, the antagonist affinity should be independent of the agonist used. Agents that show a slope of unity in the Schild plot are considered competitive antagonists of that particular receptor subtype, whereas agents that show a slope different from unity are considered non-competitive antagonists (Schild, H. O. (1947). pA, A new scale for the measurement of drug antagonism. Br. J. Pharmacol. 2, 189–206). For purposes of this disclosure, antagonists are not considered antagonists if they exhibit less than 25% blockade of phenylephrine agonism.

Biological Assays

Rabbit Urethra α1A subtype

Female New Zealand white rabbits (1.75–3.5 kg) were sacrificed by means of an I.P. injection of pentobarbital solution, 0.5 ml/kg, Somlethal®, J. A. Webster Inc., Sterling Mass. The urethra was removed with the urinary bladder and immediately placed into Krebs Ringer bicarbonate solution with the following mM concentrations: 120 NaCl, 18.0 $NaHCO_3$, 11.0 dextrose, 4.7 KCl, 2.5 $CaCl_2$, 1.5 $MgSO_4$, 1.2 $KH_2PO_4$ and equilibrated with 5% $CO_2$: 95% $O_2$. The pH was adjusted to 7.2 at 25° by titrating with a saturated solution of $NaHCO_3$. The pH increased to 7.4 at 37° C. Propranolol (0.004 mM) was included in all of the assays to block β-adrenoceptors. The urethra was separated from the bladder and cut into 4 tissue rings approximately 3–4 mm wide. One end was fixed to a stationary glass rod and the other to a Grass FT03 transducer at a basal preload of 1.0 g of tension. Data was recorded on a Grass model-7 polygraph. Tissues were rinsed every 10 minutes for a total of 45–60 minutes. The urethra was primed once with 80 mM KCl, rinsed to basal tension and again with 10 μM phenylephrine (PE). After an additional 60 minute equilibration period a reference concentration response curve was generated for each tissue using PE as the reference agonist. A cumulative concentration protocol was employed. Following a 75 minute washout period a second response curve was then generated in the same fashion using the test agent. The amount of agent necessary to cause a 50% response ($ED_{50}$) was calculated using "AGANTG" (Zielinski, P. J., Buckner, S. A. (1998). AGANTG: A Microsoft Excel 5.0-visual basic routine for the analysis of dose-response data. Analyst. 123, 1661–1668), a four parameter curve fitting program similar to "Allfit" (DeLean, A., Munson, P. J., Rodbard, D. (1980). Simultaneous analysis of families of sigmoidal curves: application to bioassay, radioligand assay, and physiological dose-response curves. Am. J. Physiol. 235, E97–102). Agonist potencies were indexed to PE and expressed as the negative logarithm ($pD_2$). Each tissue was used for only one test agonist. For antagonists, the test agent was allowed a 30 minute exposure time before a second PE curve was started. The potency, expressed as a $pA_2$, was calculated according to the method of Arunlakshana, O., Schild, H. O. (1959), Some quantitative uses of drug antagonists. Br. J. Pharmacol. 14,48–58. The individual tissues were exposed to only one concentration of the test antagonist. The regression lines of the Schild plots were analyzed using least squares regression (Snedecor, G. W., Cochran, W. G., (1980). In Statistical methods, $7^{th}$ edition, Iowa State University Press, Ames, Iowa).

Rat Spleen α1A Subtype

Male Sprague Dawley rats (150–200 g) were sedated with $CO_2$ and decapitated. The entire spleen was removed and immediately placed into Krebs Ringer bicarbonate solution as described above. The spleen was split longitudinally into two preparations per rat. One end was fixed to a stationary glass rod and the other to a Grass FT03 transducer at a basal preload of 1.0 g (Aboud R, Shafli M and Docherty J R (1993). Investigation of the subtypes of alpha-1-adrenoceptors mediating contractions of rat aorta, vas deferens, and spleen. Br J Pharmacol 109:80–87). Experimental protocol and data analysis was performed as described above followed.

Rat aorta α1D subtype:

Male Sprague Dawley rats (350–450 g) were sedated with $CO_2$ and decapitated. The entire thoracic aorta was removed and immediately placed into Krebs Ringer bicarbonate solution as described above. The aorta was cleaned of extraneous tissue and the endothelium removed by passing a 100 mm length of PE- 160 tubing through the lumen. The aorta was cut into 3–4 mm rings and mounted in 10 ml isolated tissue baths at 37° C. The aorta from each rat could supply 8 tissue rings. One end was fixed to a stationary glass rod and the other to a Grass FT03 transducer at a basal preload of 1.0 g. Absence of functional endothelium was confirmed by loss of the acetylcholine-induced (10 μM) relaxation performed at the end of the PE prime step. Experimental protocol and data analysis was performed as described above.

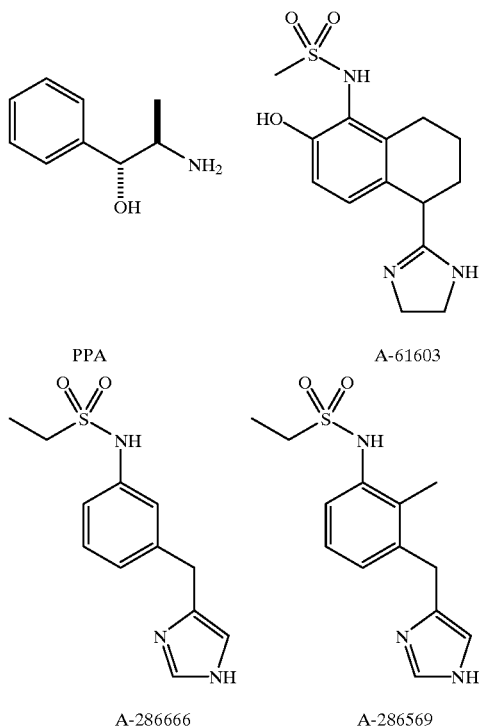

Radioligand Binding Ki (nM)

Compounds (PPA, A-61603, A-286666, and A-286569) were evaluated in radioligand binding assays specific for $α_{1A}$ (rat submaxillary gland), $α_{1b}$ (hamster receptor expressed in mouse fibroblasts) and $α_{1d}$ (rat receptor expressed in mouse fibroblasts) using [$^3$H]-prazosin as the radioligand as described in Knepper, et al. J. Pharmr Exp. Ther. (1995), 274, 97–103. The results are shown in Table 1. Radioligand binding studies indicate that PPA is a weak adrenergic ligand, while the other compounds show potent binding to the $α_{1A}$ subtype, and some show potent binding to the $α_{1b}$ and $α_{1d}$ subtypes.

TABLE 1

| Compound | $α_{1A}$ (Rat) | $α_{1b}$ (Hamster) | $α_{1d}$ (Rat) |
| --- | --- | --- | --- |
| PPA | >10,000 | >10,000 | >10,000 |
| A-61603 | 15 ± 4 | 1,210 ± 257 | 1557 ± 169 |

TABLE 1-continued

| Compound | $\alpha_{1A}$ (Rat) | $\alpha_{1b}$ (Hamster) | $\alpha_{1d}$ (Rat) |
|---|---|---|---|
| A-286666 | 137 ± 15 | 913 ± 135 | 287 ± 41 |
| A-286569 | 150 ± 32 | >10,000 | 840 ± 78 |

Evaluation of Adrenergic Compounds as Agonists

The functional activity of the ligands as adrenergic agonists was evaluated in 3 tissue bath preparations (Table 2) indicative of $\alpha_{1A}$, $\alpha_{1B}$ and $\alpha_{1D}$ subtypes. PPA is a weak agonist at all adrenergic subtypes. A-61603 is an agonist at the 3 subtypes; it is a potent agonist at the $\alpha_{1A}$ subtype (pD2=8.0) and shows selectivity towards the $\alpha_{1B}$ and $\alpha_{1D}$ subtype (30-fold or greater). A-286666 and A-286569 are agonists at the $\alpha_{1A}$ subtype (pD2=6.2 and 5.6 respectively), but they are inactive at the $\alpha_{1B}$ and $\alpha_{1D}$ subtypes (showing less than 15% activity). The efficacy of the compounds are compared as a percent of phenylephrine (100%) contraction.

TABLE 2

| | $\alpha_{1A}$ | | $\alpha_{1B}$ | | $\alpha_{1D}$ | |
|---|---|---|---|---|---|---|
| | pD$_2$ | efficacy | pD$_2$ | efficacy | pD$_2$ | efficacy |
| PPA | 3.7 | 68% | 3.6 | 34% | 4.2 | 91% |
| A-61603 | 8.0 | 88% | 6.5 | 91% | 5.6 | 100% |
| A-286666 | 6.2 | 80% | inactive | | inactive | |
| A-286569 | 5.6 | 69% | inactive | | inactive | |

Evaluation of A-286666 and A-286569 as Antagonists

Although some of these compounds show binding at the $\alpha_{1B}$ and $\alpha_{1D}$ subtypes, the binding was not reflected as functional agonism. Therefore, A-286666 and A-286569 were tested as antagonists on these tissue preparations (Table 3). Studies were conducted in tissue bath assays that determine effect on $\alpha_{1B}$ and $\alpha_{1D}$ adrenergic receptor subtypes. Once again, phenylephrine was used to generate a contraction curve and compared to the test compound to see if contraction was blocked with the test compound. Based on the slope and regression (r) analysis, it was determined that A-286666 is a competitive antagonist at the $\alpha_{1B}$ and $\alpha_{1D}$ subtypes (pA2=5.8 and 6.5, respectively). A-286569 behaves as a non-competitive antagonist at the $\alpha_{1B}$ receptor and at the $\alpha_{1D}$ receptor subtypes, as indicated by the Schild plot analysis (due to the poor regression correlation).

TABLE 3

| | $\alpha_{1B}$ | | | $\alpha_{1D}$ | | |
|---|---|---|---|---|---|---|
| | pA$_2$ | slope | r | pA$_2$ | slope | r |
| A-286666 | 5.8 | 0.81 | 0.9 | 6.5 | 0.93 | 0.9 |
| A-286569 | 4.8 | 1.3 | 0.6 | 5.2 | 1.1 | 0.5 |

Evaluation of IUP/MAP

Intraurethral Pressure in Dogs (IUP-MAP test)

Female Beagle dogs (Marshall Farms, North Rose, N.Y.) greater that 2 years of age and weighing between 12 and 15 kg were used in these studies. At least 2 weeks prior to any agonist dosing, dogs were instrumented for the chronic measurement of arterial blood pressure by implanting a telemetry transducer/transmitter (TA11PA-C40, Data Sciences International, St. Paul, Minn.) into a carotid artery.

On the test day, dogs fasted since the previous afternoon were pre-anesthetized with thiopental sodium 15 mg/kg i.v (Pentothal™, Abbott) and intubated. Anesthesia was maintained by allowing the dog to spontaneously breathe a mixture of isoflurane (2.5 to 3 volume %) and oxygen delivered by a Narkomed Standard anesthesia system (North American Drager, Telford, Pa.). An Abbocath-T™ i.v. catheter (18-G, Abbott Laboratories, Abbott Park, Ill.) was inserted into the cephalic vein for the administration of agonists. A telemetry receiver (RA1310, DataSciences) was placed under the head of each dog and was interfaced to a computerized data acquisition system (Modular Instruments Inc.(MI2), Malvern, Pa.) which allowed for the continuous calibrated recording of arterial blood pressure which was electronically filtered to determine its mean value (MAP).

Intraurethral pressure was monitored using a balloon catheter technique previously described (Brune et al., Drug Development Research 34:267–275,1995). Briefly, a 7 Fr catheter balloon catheter (41224-01, Abbott) was inserted into the urethral orifice and advanced approximately 15 cm until the tip was well inside the bladder. The balloon was then inflated with 1 ml of room air and the catheter slowly withdrawn until resistance (corresponding to the bladder neck) was evident. The balloon was then deflated and the catheter withdrawn an additional 2 cm. The balloon was then reinflated and its catheter port connected to a Gould Statham P23Dd pressure transducer interfaced to a computerized data acquisition system (Modular Instruments, Inc., Malvern, Pa.) for the measurement of intraurethral pressure (IUP). The MAP and IUP pressor responses to increasing iv doses of test agonists were obtained simultaneously. The pressor effects of each dose were allowed to return to baseline before the next dose was given. For PPA, eight dogs (n=8) were used while for A-61603, A-286666, and A-286569, four dogs were used for each agonist (n=4).

The dose required to elicit significant and clinically meaningful changes in IUP (5 mm Hg) relative to the dose required to elicit a physiologically significant increase in blood pressure (20 mm Hg) is calculated. Clinical studies have demonstrated a significant reduction in incontinent episodes in SUI patients after a 5 mmHg increase in urethral pressure (Collste L and Lindskog M (1987). Phenylpropanolamine in treatment of female stress incontinence. *Urology* 30: 398–403; Wein A (1995). Pharmacology of incontinence. *Urologic Clinics of North America* 22: 557–577).

Evaluation of the Adrenergic Agents in vivo

Examples of compounds with improved in vivo uroselectivity versus PPA and A-61603 are A-286666 and A-286569. IUP and MAP pressor effects of each agonist dose were expressed as the maximum net change in each pressure over pre-dose baseline levels. Subsequently, the effective doses required to produce a 5 mmHg increase in IUP (IUP ED$_{5mmHg}$) and a 20 mmHg increase in MAP (MAP ED$_{20mmHg}$) were estimated from the dose response data from each dog. Relative urethral versus vascular selectivity of each agonist in each dog was estimated using a ratio of these respective potency indices (MAP ED$_{20mmHg}$/IUP ED$_{5mmHg}$).

PPA, A-61603, A-286666 and A-286569 caused dose-dependent increases in both intraurethral pressure and mean arterial pressure (FIGS. 1–4). However, there were marked differences in urethral selectivity of these four compounds. While PPA and A-61603 showed no urethral selectivity versus the vascular bed (0.4 and 1.7, respectively), A-286666 and A-286569 were the most selective compounds in the in vivo model (Table 4) as they show 3-fold or more selectivity ratio. The selectivity ratio was calculated for each dog and then averaged. This indicated a need for $\alpha_{1A}$ adrenoceptor agonist and an $\alpha_{1B}$ antagonist action in the body to increase urethral smooth muscle contraction while avoiding hypertension caused by vascular tissue contraction. In addition, an $\alpha_{1D}$ antagonist may provide antagonistic actions in the bladder.

Data are expressed as means (±S.E.M) and all doses are in nmol/kg, i.v.

TABLE 4

|  | MAP ED20 mmHg | IUP ED5 mmHg | Selectivity ratio MAP ED20/IUP ED5 |
|---|---|---|---|
| PPA | 331 ± 80 | 1092 ± 384 | 0.4 |
| A-61603 | 0.27 ± 0.05 | 0.16 ± 0.02 | 1.7 |
| A-286666 | 80.4 ± 14 | 12.1 ± 1.5 | 6.5 |
| A-286569 | 201.6 ± 67 | 41.9 ± 6.2 | 5.6 |

What is claimed:

1. A method of treating stress urinary incontinence by administering a compound that is an $\alpha_{1A}$ adrenoceptor agonist and an $\alpha_{1B}$ antagonist.

2. A method of claim 1 wherein said compound is an α1D antagonist.

3. A method of claim 1 wherein said $\alpha_{1B}$ antagonism is competitive.

4. A method of claim 1 wherein said $\alpha_{1B}$ antagonism is non-competitive.

5. A method of claim 1 wherein said compound has an IUP (5 mmHg)/MAP (20 mmHg) selectivity ratio of 5 or greater.

6. A method of claim 1 wherein said compound has an IUP (5 mmHg)/MAP (20 mmHg) selectivity ratio of 10 or greater.

* * * * *